United States Patent [19]

Taheri

[11] Patent Number: 5,117,007
[45] Date of Patent: May 26, 1992

[54] CONTINUOUS PROCESS FOR THE PRODUCTION OF MALEIC ANHYDRIDE FROM A C$_4$-HYDROCARBON FEEDSTOCK

[75] Inventor: Hassan Taheri, Naperville, Ill.

[73] Assignee: Amoco Corporation, Chicago, Ill.

[21] Appl. No.: 464,286

[22] Filed: Jan. 12, 1990

Related U.S. Application Data

[63] Continuation-in-part of Ser. No. 305,798, Feb. 2, 1989, abandoned, which is a continuation-in-part of Ser. No. 91,440, Aug. 31, 1987, abandoned.

[51] Int. Cl.$^5$ ............................................. C07D 307/60
[52] U.S. Cl. ..................................... 549/259; 549/260
[58] Field of Search ................................ 549/259, 260

[56] References Cited

U.S. PATENT DOCUMENTS 4,515,899  5/1985  Click et al. .......................... 549/260
4,701,433  10/1987  Edwards ............................. 549/259

FOREIGN PATENT DOCUMENTS 0174173  3/1986  European Pat. Off. .
1464198  2/1977  United Kingdom .

*Primary Examiner*—Bernard Dentz
*Attorney, Agent, or Firm*—Gunar J. Blumberg; William H. Magidson; Robt. J. Wagner

[57] ABSTRACT

A continuous process is disclosed for the production of maleic anhydride by the partial oxidation of a hydrocarbon feedstock comprising n-butane in a concentration of at least 1.6 mole percent wherein a mixture of the feedstock and an oxidizing medium is contacted with a vanadium-phosphorus-oxygen catalyst wherein a solution of water and an alkyl ester of orthophosphoric acid is continually added to said feedstock, wherein ratio of water to elemental phosphorus in said alkyl ester is in the range of from about 6500:1 wt. to about 50,000:1 wt., water to phosphorus, and the differences in reaction temperature throughout the entire reaction zone is less than about 45° C. (80° F.).

4 Claims, 4 Drawing Sheets

CONTINUOUS PROCESS FOR THE PRODUCTION OF MALEIC ANHYDRIDE FROM A C₄-HYDROCARBON FEEDSTOCK

CROSS-REFERENCE TO RELATED APPLICATION

This is a continuation-in-part of Ser. No. 305,798, filed Feb. 2, 1989, which in turn is a continuation-in-part application of Application U.S. Ser. No. 091,440, filed on Aug. 31, 1987, both now abandoned.

FIELD OF THE INVENTION

This invention relates to a continuous process for the production of dicarboxylic acid anhydrides by the partial oxidation of aliphatic hydrocarbons. More particularly, this invention is directed to a continuous process for the production of maleic anhydride by the partial oxidation of aliphatic hydrocarbons having four carbon atoms in a nearly isothermal reaction zone, in the presence of a phosphorus-vanadium-oxygen type catalyst wherein water and a phosphorus compound, in a weight ratio of at least 6500:1, are added simultaneously to a feedstock of an aliphatic hydrocarbon, wherein the aliphatic hydrocarbon is present in an amount of at least 1.6 mole percent.

BACKGROUND OF THE INVENTION

Large quantities of maleic anhydride are produced each year throughout the world, since maleic anhydride can be employed as a versatile intermediate for chemical synthesis and is often used in the production of alkyl resins. In the past, maleic anhydride was produced commercially by either the catalytic oxidation of benzene or the catalytic oxidation of butenes. An important method formerly employed commercially for the manufacture of maleic anhydride consisted of air oxidation of benzene in the presence of a heavy metal oxide catalyst. Since benzene fumes are toxic and since the use of butane is more economical than benzene, the trend has been to minimize or eliminate the use of benzene as a feedstock and to oxidize either butenes or butane to maleic anhydride.

A typical catalyst that can be used for the oxidation of butane to maleic anhydride is a catalyst comprising the oxides of vanadium and phosphorus. For example, in U.S. Pat. No. 3,293,268, Bergman, et al., teach that the oxidation of n-butane or other saturated aliphatic hydrocarbons having from 4 to 10 carbon atoms can be performed under controlled temperature conditions in the presence of a specified class of phosphorus-vanadium-oxygen-containing complex catalysts. While such a catalyst is capable of oxidizing butane, it does not give sufficiently high yields.

Attempts have been made to overcome this disadvantage by employing various activators, stabilizers, and promoters in the catalyst in order to improve the yields of maleic anhydride. For example, in U.S. Pat. No. 3,862,146, Boghosian discloses the oxidation of n-butane to maleic anhydride in the presence of a phosphorus-vanadium-oxygen complex catalyst containing zinc, bismuth, copper, or lithium as an activator. Raffelson, et al., teach the use of such catalyst components in U.S. Pat. No. 3,867,411; Young, et al., in U.S. Pat. No. 3,888,886; and Higgins, et al., in U.S. Pat. No. 4,147,661. Unfortunately, the phosphorus-vanadium-metal-promoted catalysts tend to lose selectivity rather rapidly. This necessitates the reactivation or regeneration of these catalysts. In U.S. Pat. Nos. 4,020,174; 4,094,816; and 4,089,807; the patentees teach that a vanadium-phosphorus-metal-promoted catalyst can be reactivated by the use of carbon tetrachloride. In U.S. Pat. Nos. 3,296,282 and 3,474,041, the patentees disclose the process of treating a vanadium-phosphorus oxidation catalyst with a phosphine, phosphite, or phosphonate by periodically or continuously passing such phosphorus compound to the reactor, either with or without interrupting the olefin feed flow that is being used to make the maleic anhydride. United Kingdom Patent Specification 1,464,198 discloses the reactivation or regeneration of certain vanadium-phosphorus-oxygen catalyst complexes promoted with zirconium, hafnium, chromium, iron, lanthanum, or cerium by having the catalyst contacted during vapor-phase oxidation with an alkyl ester of orthophosphoric acid having the formula $(RO)_3P=O$, wherein R is hydrogen or a $C_1$ to $C_4$ alkyl radical, at least one R being a $C_1$ to $C_4$ alkyl radical.

In U.S. Pat. No. 4,701,433, Edwards discloses a process for the manufacture of maleic anhydride from butane in the presence of a vanadium-phosphorus-oxygen catalyst or a vanadium-phosphorus-oxygen-co-metal catalyst, wherein water and a phosphorus compound are added to the reaction system to reversibly deactivate a portion of the catalyst in the catalyst bed containing a reaction exotherm (hot spot) prior to the addition of the phosphorus compound, which addition of phosphorus compound moves the reaction exotherm downstream into the catalyst bed, and an improved catalyst bed is obtained when the partially deactivated catalyst in the original "hot spot" location reactivates to produce a more isothermal catalyst bed.

Although Edwards, et al. recognized the utility of a more isothermal catalyst bed to improve yield, Edwards accomplished a more isothermal catalyst bed temperature by shifting the location of the original "hot spot" to a new location and then reactivating the old location. Edwards teaches that improvement in yield can be obtained as long as there is sufficient catalyst bed into which the exotherm may migrate. Edwards failed to recognize that constant shifting of the exotherm is inherently unstable and not suitable for long-term operation.

U.S. Pat. No. 4,780,548, Edwards, et al. teaches a continuous process for the vapor-phase oxidation of a n-butane feedstock to form maleic anhydride in which n-butane is contacted in the presence of molecular oxygen or air at an hourly space velocity of about 100 to about 4000 cubic centimeters of feed per cubic centimeter of catalyst per hour with a vanadium-phosphorus-oxygen catalyst wherein the catalyst is regenerated continuously or batchwise by contacting it during the vapor phase oxidation with an alkyl ester of orthophosphoric acid having the formula $(RO)_3P=O$ where R is hydrogen or a $C_1$ to $C_4$ alkyl, at least one R being a $C_1$ to $C_4$ alkyl, wherein the amount of water added is about 1000 parts per million to about 40,000 parts per million by weight of the reactor feed gas stream and the amount of the alkyl ester added is about 0.1 parts per million to about 100,000 parts per million by weight of the reactor feed gas stream. The gaseous feed stream to the reactor will contain from about 0.2 to about 1.7 mole % of n-butane but about 0.8 to about 1.5 mole % of n-butane is satisfactory for optimum yield from the process of the invention. Edwards teaches that higher concentrations can be employed but explosive hazards may be encountered. Even though Edwards acknowledged that explosive mixtures could be employed, above 1.5-1.7 moles n-butanes, Edwards did not recognize that an isothermal reaction employing a higher concentration of n-butane would result in a yield continuously maintained at a high level for extended periods of time despite the possibility of explosive hazards.

Becker, et al., U.S. Pat. No. 4,795,818 disclosed a method for optimizing the yield of a vanadium-phosphorus catalyst during the oxidation of n-butane to maleic anhydride, wherein a volatile phosphorus compound is continuously added at a rate selected to maintain maximum yield while holding the operating temperature constant, the operating temperature being monitored preferably by the outlet gas temperature. Becker et al., indicate that the amount of phosphorus compound to be added should be sufficient to prevent decline in operating temperature. Becker, et al., fail to recognize the impact of the water added to the reaction and rely only on the addition of a volatile phosphorus compound to the process.

In U.S. Pat. No. 4,515,899, Click, et al., teach that the useful life of a vanadium-phosphorus-oxygen catalyst can be extended in fixed bed reactors by treatment with a phophorus compound followed by steam treatment and furnish data showing movement of the exotherm further into the catalyst bed.

In the partial oxidation of n-butane to maleic anhydride, the reaction is highly exothermic and a catalyst hot spot temperature can develop with potential of a runaway oxidation reaction and consequent complete loss of product yield. Such a development of a hot spot temperature is potentially extremely detrimental to the progress of the oxidation reaction. The hot spot temperature readily occurs in the oxidation and is quite sensitive to variations in the concentration of feed hydrocarbon. Small increases in the concentration of the hydrocarbon feed can result in large increases in hot spot temperature and a concurrent decrease in selectivity and yield. In addition, high hot spot temperatures can shorten the useful life of the catalyst being employed. It is therefore necessary to avoid the development of an excessively high hot spot temperature and to maintain an isothermal catalyst temperature range over the entire length of the reaction zone to obtain consistent high yield and lengthened catalyst life. Also, consistent high product yield requires a process with consistent process parameters.

It has now been found that the beneficial effect of adding a phosphorus compound in water, in certain ratios to each other, to control the reaction temperature profile in oxidation of n-butane to maleic anhydride can be obtained over the entire reaction zone of a fixed bed reactor. The beneficial effect occurs over the entire reaction zone including the so-called hot spot temperature zone but also a significant beneficial effect of the reaction temperature profile has been found to result despite operation in the flammability zone which exists wherein concentration of n-butane in the feed is about 1.7 mole %, or higher, and air is the source of oxygen. The required ratio of water to phosphorus in the phosphorus compound relates to the concentration of n-butane, and also to the reactor size and shape. An isothermal reaction zone temperature thereby results wherein the reaction zone temperature gradient is within a maximum range of about 45° C. (80° F.) with consequent increase in overall yield.

It has now been found that an isothermal reaction zone temperature wherein n-butane concentration in the feedstock is greater than 1.6 mole percent results in consistent high yield of maleic anhydride. The continuous addition of a phosphorus-water solution to the reaction in an essential ratio of phosphorus to water causes the effect of the addition to occur over the entire reaction zone of the reactor to decrease the so-called hot spot temperature and increase the over-all reaction temperature throughout the reaction zone to result in an isothermal reaction zone, which includes the so-called hot spot, wherein the temperature gradient in the reaction zone is within the range of about 45° C. (80° F.).

SUMMARY OF THE INVENTION

The instant invention comprises a continuous process for vapor-phase oxidation of a feedstock containing at least 1.6 mole % of n-butane to prepare maleic anhydride in the presence of a vanadium-phosphorus-oxygen catalyst and an oxidizing medium comprising a member selected from the group consisting of molecular oxygen, air, and an oxygen-containing gas wherein a solution of a phosphorus compound in water is continuously added to the feedstock, wherein the weight ratio of water to phosphorus is in the range of from about 6500:1 to about 50,000:1, and the temperature gradient of the isothermal oxidation reaction zone temperature throughout the entire effective reaction zone is less than about 45° C. (80° F.). The result of the consistently uniform isothermal method of operation is a consistent uniformly high yield of product using catalysts which have been in use for long periods of time.

DESCRIPTION OF THE DRAWINGS

The accompanying drawings depict the catalyst bed temperature profiles obtained after water-phosphorus additions in the form of a water and triethyl phosphate (TEP) solution to the oxidation reaction of n-butane in the presence of a vanadium-phosphorus-oxygen catalyst.

DETAILS OF THE INVENTION

Figure 1:
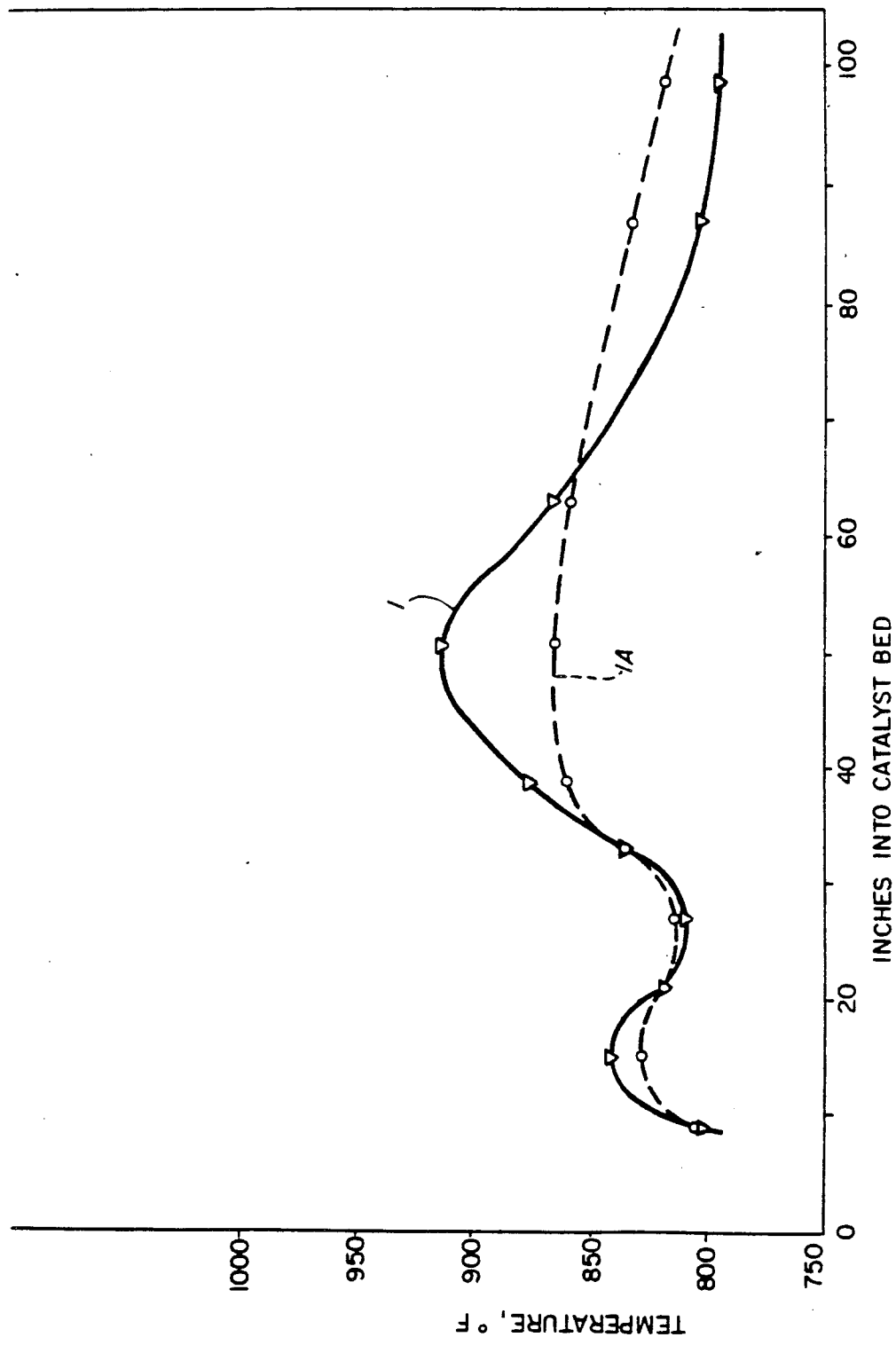
FIG. 1 illustrates two temperature profiles over the catalyst bed. Temperature profile 1 illustrates a reaction zone temperature profile wherein an excessive hot spot exotherm occurs over the first portion of the catalyst bed and reaction zone temperature decreases precipitously following the exotherm and overall reaction zone temperature gradient is within the range of 65° C. (117° F.). Temperature profile 1A illustrates a more preferred isothermal temperature gradient range of 33° C. (60° F.).

In the process of the instant invention, maleic anhydride is produced by the partial oxidation of n-butane. In general, catalysts utilized for the oxidation of n-butane to maleic anhydride are based on vanadium and phosphorus. Various metal activators have been used to enhance the phosphorus-vanadium catalyst. The difficulty with the phosphorus-vanadium metal-produced catalysts is that they tend to lose selectivity quite quickly. In this connection, U.S. Pat. Nos. 4,020,174; 4,094,816 and 4,089,807 teach that carbon tetrachloride can be used to reactivate the vanadium-phosphorus metal-produced catalyst. In U.S. Pat. No. 3,296,282 and U.S. Pat. No. 3,474,041 there is described a method for the regeneration of vanadium-phosphorus oxidation catalysts used in the oxidation of olefins to make maleic anhydride. These references disclose the process treating the catalyst with a phosphine, phosphite or phosphonate by periodically or continuously passing the phosphorus compound to the reactor, with or without interrupting the olefin feed flow. British Patent Specification No. 1,464,198 teaches regeneration of phosphorus complexes with certain phosphates. This reference does not disclose the reactivation of vanadium-phosphorus catalysts by addition of a phosphorus compound in the presence of water solution in a synergistic ratio in the feed gas stream. Particularly, the reference does not appreciate that a ratio of water to phosphorus in the feed gas stream is required to control the development of a runaway hot spot temperature and to obtain a more isothermal reaction zone temperature.

European Patent Application 85306209.9 teaches a method of optimizing the yield of a vanadium-phosphorus catalyst during the oxidation of n-butane to maleic anhydride which comprises establishing the temperature at which the catalyst provides the desired percentage conversion and yield of maleic anhydride with the established feed composition and maintaining that temperature by continuously introducing an amount of a phosphorus compound necessary to prevent a decline in selectivity to maleic anhydride without significantly increasing the temperature. Salt bath temperature range was from 340° to 450° C. This reference does not disclose the critical synergism in the amounts of water and organic phosphate added to the reaction, and this reference does not teach the activity of the reactor temperature being in the range of greater that 425° C. and less than about 475° C. to obtain a high yield. Maximum yield reported by this reference was 87 wt. % at a salt bath temperature of 414° C. A salt bath temperature of 430° C. was termed excessive.

I have discovered a method for isothermally stabilizing the reaction temperature in the vapor phase oxidation in a fixed bed reactor of a feedstock containing at least 1.6 mole percent n-butane to maleic anhydride in the presence of a vanadium-phosphorus-oxygen catalyst over a long period of time. According to my process, the vapor-phase oxidation of n-butane in a fixed bed reactor is conducted by contacting the n-butane feedstock containing an essential ratio of water and organic phosphorus compound with a source of oxygen in the presence of a vanadium-phosphorus-oxygen catalyst wherein the reaction zone temperature is maintained within an isothermally stable temperature gradient range of about 45° C. (80° F.).

As is taught in the prior art, see British Patent Specification No. 1,464,198; U.S. Pat. Nos. 3,296,282; 3,474,041; 4,780,548; 4,701,433; and European Application No. 85306209.9, the addition of a phosphorus compound to the vanadium-phosphorus-oxygen catalyst can act to regenerate the catalyst either in batch or continuous method during the vapor-phase oxidation of butane and other $C_4$ hydrocarbons. However, prior investigators have failed to appreciate the significance of the relationship of water and an organic phosphorus compound engendered at the reaction temperature of the oxidation reaction when the water and organic phosphorus compound are continuously fed in an essential ratio to the reaction as components of the feedstock in a fixed bed reactor. The organic phosphorus compound in the instant invented process is an alkyl ester of orthophosphoric acid having the formula $(RO)_3P=O$, wherein R is hydrogen of a $C_1$ to $C_4$ alkyl, at least one R being a $C_1$ to $C_4$ alkyl.

In the process of the instant invention, the catalyst can be employed in one or more fixed beds. The size and shape of such fixed bed catalyst are not critical, i.e., the catalyst can be in the shape of a cylinder, either solid or hollow, or any other suitable shape.

The catalyst can be prepared in various ways including the ones disclosed in U.S. Pat. Nos. 3,862,146; 4,418,003; 4,416,802; and 4,416,803. Other ways to prepare the catalyst are disclosed in U.S. Pat. No. 4,328,126 wherein the catalyst is made from an organic solvent system. Precipitation of the phosphorus-vanadium oxide can suitably be effected by azeotropic distillation of the organic solvent. The atomic ratio of vanadium to phosphorus can suitably be in the range of about 0.5:1 to about 1.25:1, preferably in the range of about 0.6:1 to about 1:1. The atomic ratio of phosphorus to vanadium is suitably in the range of about 2:1 to about 0.8:1, preferably about 1:1 to about 1.7:1.

The ratio of water to phosphorus added continuously to the reaction is in the range of from about 6500:1 to about 50,000:1. Below the 6500:1 ratio, there is a tendency for the exotherm to progress throughout the bed of the catalyst reaction zone, as is taught in Edwards, U.S. Pat. No. 4,780,548. Above the ratio of 50,000:1, there is a tendency for a runaway exotherm to occur at high concentrations of n-butane in the reaction zone.

The oxidation reaction can be conducted at a temperature within the range of from about 425° F. (797° F.) to about 470° C. (878° F.) preferably from about 425° F. (797° F.) to about 460° C. (870° F.). The alkyl phosphate in a water medium is contacted with the feed gas stream flowing to the reactor. If desired, the water and alkyl phosphate may be added separately to the feed gas stream instead of as a solution. Alternatively, the alkyl phosphate and water may be added directly to the butane and air reactants. Air is entirely satisfactory as a source of oxygen, but synthetic mixtures of oxygen and diluent gases such as nitrogen may also be employed. Air enriched with oxygen may be used.

The gaseous feed stream to the oxidation reactors will normally contain air and about 1.6 to about 2.4 mole percent of n-butane for maximum yield. About 1.6 to about 2.1 mole percent of n-butane is satisfactory for 90 to 95% yield of maleic anhydride by the process of this invention. Lower concentrations of butane, less than about 1.6 mole percent, will reduce the total yield obtained at equivalent flow rates and, thus, are not desirable for economic reasons. The flow rate of the gaseous stream through the reactor may be varied within rather wide limits, but the preferred range of operations is at the rate of at least about 1250 VHSV, $hr^{-1}$. Lower flow rates or high n-butane concentrations cause runaway exotherms. The ratio of water to the phosphorus as alkyl phosphate is about 6500:1 to about 50,000:1 by weight. The preferred water-phosphorus ratio is about 6500:1 to about 35,000:1 by weight. Residence times of the gas stream will normally be less than about four seconds, more preferably less than about one second, and down to a rate where less efficient operations are obtained. The flow rates and residence times are calculated at standard conditions of 760 mm of mercury and at 0° C.

A variety of reactors will be found to be useful and multiple tube heat exchanger-type reactors are quite satisfactory. The tubes of such reactors may vary in outside diameter from about three-quarter inch to about 1½ inches inside, inside diameter from 0.67 inches to 1.01 inches, and the length may be varied from about three to about ten or more feet. The oxidation reaction is an exothermic reaction and, therefore, relatively close control of the reaction temperature is maintained. It is desirable to have the surface of the reactors at a relatively constant temperature and some medium is needed to conduct heat from the reactors, such as lead and the like, but it has been found that eutectic salt baths are completely satisfactory. One such salt bath is a sodium nitrate, sodium nitrite, and potassium nitrate eutectic constant temperature mixture. An additional method of temperature control is to use a metal block reactor whereby the metals surrounding the tube act as a temperature regulating body. As will be recognized by one skilled in the art, the heat exchanger medium may be kept at the proper temperature by heat exchangers and the like. The reactor or reaction tubes may be iron, stainless steel, carbon steel, nickel, glass tubes such as vycor, and the like. Both carbon steel and nickel tubes have excellent long life under the conditions of the reaction described herein. Normally, the reactors contain a preheat zone containing an inert material such as one-quarter inch Alundum(TM) pellets, inert ceramic balls, nickel balls, or chips and the like present at about one-half to one-tenth the volume of the active catalyst present.

The temperature of reaction is within a critical range. The oxidation reaction is exothermic and once reaction is underway, the main purpose of the salt bath or other media is to conduct heat away from the walls of the reactor. Better operations are normally obtained when the reaction temperature employed is no greater than about 30° to about 50° F. above the salt bath temperature. The temperature of the reactor, of course, will also depend to some extent upon the size of the reactor, the hydrocarbon feedstock concentration, the concentration of the water and alkyl phosphate in the feedstock and the ratio of water to alkyl phosphate in the feedstock.

The process of the instant invention is a continuous process because of the necessity of continuously adding a water-phosphorus solution to continuously and isothermally stabilize the process reaction temperature throughout the reaction zone.

The reaction may be conducted at atmospheric, super-atmospheric or below atmospheric pressure. The exit pressure will be at least slightly higher than ambient pressure to ensure a positive flow from the reactor. The pressure of the inert gases must be sufficiently higher to overcome the pressure drop through the reactor.

Maleic anhydride may be recovered by a number of ways well known to those skilled in the art. For example, the recovery may be by direct condensation or by absorption in suitable media and purification of the maleic anhydride.

The following examples will serve to provide a fuller understanding of the invention, but it is to be understood that these examples are given for illustrative purposes only and should not be interpreted as limiting the invention in any way. In the examples, the terms "conversion", "selectivity" and "yield" are defined as follows:

$$\text{Conversion \%} = \frac{\text{moles n-butane reacted}}{\text{moles n-butane in feed}} \times 100$$

$$\text{Selectivity \%} = \frac{\text{moles maleic anhydride produced}}{\text{moles n-butane feed consumed}} \times 100$$

$$\text{Yield Wt \%} = \text{Conversion} \times \text{Selectivity} \times 169$$

In Examples 1-3, the data were gathered using catalyst which had been on stream between 2,500 to 3,300 hours. In Example 4, the catalysts had been on stream between 4235 to 5669 hours. The invented method accordingly is demonstrated as stabilizing the reaction temperature in a vapor-phase oxidation in a fixed bed reactor of a n-butane feedstock to maleic anhydride in the presence of a vanadium-phosphorus-oxygen catalyst wherein the catalyst has been in use over a long period of time.

EXAMPLE 1

This example was carried out to show the effect of n-butane concentration on the hot spot temperature and performance of an oxidation catalyst when employed to convert n-butane to maleic anhydride.

These tests, as well as those discussed in the following examples, were conducted in a continuous oxidation pilot unit equipped with a reactor tube having a length of 16 ft., an outside diameter of 1 in., and an inside diameter of 0.882 in and a continuous product recovery and gas chromatographic analytical system. The reactor was surrounded by a salt bath and was equipped with a ¼-in thermowell containing 13 stationary thermocouple junctions, which were concentrated more toward the inlet of the catalyst bed, where a hot spot would normally be located. The hydrocarbon feed was n-butane stream comprising about 97 wt. % n-butane, the remainder being principally isobutane. The catalyst, identified hereinafter as Catalyst A, was a commercially-prepared oxidation catalyst obtained from the Denka Chemical Company. These tests were being conducted at the time this catalyst had been on stream for 2,500 to 3,200 hours.

The tests in this example were performed at two gas hourly space velocities, 1,350 $hr^{-1}$ and 1,600 $hr^{-1}$, and three n-butane concentrations, 1.22 mole %, 1.50 mole %, and 1.65 mole %. The salt bath was maintained at a constant temperature of 418° C. (784° F.) A pressure of 32.1 psia was employed. TEP was added at a rate to provide a concentration of 7±1 lb/10⁵ lb n-butane to maintain a concentration of 2 ppm wt phosphorus in the reactor feed. Water was added at such a rate to maintain a concentration of 7000 ppm wt in the reactor feed. The catalyst was between 2,500 and 3,000 hours on stream.

The results of these tests are presented hereinbelow in Table I. The catalyst performance parameters, i.e., conversion, selectivity, and yield, were calculated from the gas chromatographic data obtained from the particular test.

TABLE I

EFFECT OF n-BUTANE CONCENTRATION WITH CATALYST A

| VHSV, hr-1 | n-Butane, mole % | Hot Spot Temp. °C. | Hot Spot Temp. °F. | Conv, % | Selectivity, mole % | Yield, wt % |
|---|---|---|---|---|---|---|
| 1,350 | 1.22 | 458 | 856 | 87.2 | 67.7 | 99.5 |
| 1,350 | 1.50 | 479 | 894 | 84.7 | 67.0 | 95.5 |
| 1,350 | 1.65 | 526 | 979 | 88.7 | 61.5 | 92.0 |
| 1,600 | 1.22 | 462 | 864 | 82.0 | 69.5 | 96.0 |
| 1,600 | 1.50 | 484 | 904 | 81.0 | 67.5 | 92.0 |
| 1,600 | 1.65 | 518 | 964 | 82.0 | 64.5 | 89.0 |

These results indicate that at a water/phosphorus concentration of 7000/2 ppm wt., at either VHSV, an increase in the n-butane concentration causes the hot spot temperature to increase with a concomitant decrease in both selectivity and yield. Although yields of up to 99.5 wt % can be obtained with 1.22 mole % n-butane in the feed, the low concentration below 1.50 mole % reduces the total yield of maleic anhydride and thus is uneconomic.

EXAMPLE 2

This example was conducted also to demonstrate the effect of n-butane concentration on the hot spot temperature and the performance of an oxidation catalyst when employed to convert n-butane to maleic anhydride. In these tests, the catalyst was an experimental catalyst comprising vanadium, phosphorus, and oxygen modified with molybdenum. The catalyst, identified hereinafter as Catalyst B, contained 24.4 wt % vanadium, 18.3 wt % phosphorus, and 1.45 wt % molybdenum. The fresh catalyst also contained 6.29 wt % carbon, 0.35 wt % hydrogen, and 1.49 wt % chloride.

These tests were conducted at a pressure of 34.7 psia, a VHSV of 2,000 hr⁻¹, a salt bath temperature within the range of about 416° C. (780° F.) to about 417° C. (782° F.), and a moisture concentration in the feed of 11,000 ppm wt. Ratio of water to phosphorus was from 6626:1 to 4305:1. The catalyst had been on stream for 2500 to 3200 hours.

The results of these tests are presented hereinafter in Table II.

TABLE II

EFFECT OF n-BUTANE CONCENTRATION WITH CATALYST A

| n-Butane, mole % | TEP, ppm wt | Ratio H₂O:P | Hot Spot Temp. °C. | Hot Spot Temp. °F. | Conv. % | Selectivity, mole % | Yield, wt % |
|---|---|---|---|---|---|---|---|
| 1.5 | 10 | 6626:1 | 460 | 860 | 87.5 | 62.3 | 92.0 |
| 1.6 | 10 | 6626:1 | 466 | 870 | 88.0 | 61.3 | 91.0 |
| 1.7 | 10 | 6626:1 | 466 | 870 | 88.0 | 61.0 | 90.5 |
| 1.8 | 15 | 4305:1 | 477 | 890 | 86.0 | 61.3 | 89.0 |

In these tests, the lower end of the n-butane flammability range has been entered. These results, concurring with those in Example 1, show the trend that, as the n-butane concentration and phosphorus concentration are increased, the selectivity and the yield are decreased.

EXAMPLE 3

In this example, TEP concentration in the feed was increased successively at a constant feed rate and a constant moisture content of 11,000 ppm wt., when Catalyst A was employed to oxidize n-butane to maleic anhydride. The catalyst had been on stream between 3,000 hr and 4,000 hr, when it was utilized in these tests. The VHSV was 1600 hr⁻¹; the n-butane concentration 1.6 mole %; and the pressure, 32.1 psia. The results of these tests are presented in Table III.

TABLE III

EFFECT OF TEP LOADING ON HOT SPOT TEMPERATURE WITH CATALYST A

| TEP LOADING 1 lb TEP 10⁵ lb n-C4 | TEP, ppm wt | Ratio H₂O:P | Salt Bath °C. | Hot Spot Temp °C. | Hot Spot Temp °F. | Conv, % | Selectivity mole % | Yield wt % |
|---|---|---|---|---|---|---|---|---|
| 6.0 | 2 | 32,290:1 | 418 | 518 | 964 | 82.0 | 64.5 | 89.0 |
| 9.2 | 3 | 21,527:1 | 417 | 484 | 904 | 81.0 | 64.3 | 87.9 |
| 12.3 | 4 | 16,145:1 | 421 | 469 | 875 | 77.4 | 69.0 | 90.1 |
| 18.0 | 6 | 10,763:1 | 424 | 469 | 875 | 76.8 | 70.1 | 90.9 |

The data show that the hot spot temperature was reduced when the TEP concentration was increased from 2 ppm wt to 6 ppm wt. The reduced hot spot temperature provided improved catalyst selectivity and yield. However, the higher TEP loading of phosphorus relative to water content of 21,527:1 resulted in partial loss of catalyst activity. The activity decrease required higher salt bath temperatures. However, in spite of the higher salt bath temperatures, the hot spot temperature was significantly lower. Under this type of operation involving less severe conditions, the useful life of the catalyst is extended.

EXAMPLE 4

In this example, several tests were made with Catalyst A wherein different VHSV's and different n-butane concentrations were employed. The TEP concentration was held at either 9.3 lb TEP/10⁵ lb n-C₄ or 18.6 lb TEP/10⁵ lb n-C₄, while the feed moisture concentration was maintained at 15,000 ppm wt. The VHSV that was employed was within the range of about 1,250 hr⁻¹ to about 1,650 hr⁻¹, while the n-butane concentration that was employed was in the range of about 1.61 mole % to about 2.1 mole %, which butane concentration values are at the lower end of the butane flammability range. The pressure was 32.1 psia.

These tests were conducted in a single run, each test comprising a combination of selected operating conditions. The tests employing the lower TEP concentration were performed in the earlier portion of the run of 4764 hours on stream. The TEP concentration was changed to the higher value at 5,406 hr on stream; consequently, the tests conducted with the higher value were made in the later stages of the run after 5,406 hr on stream.

Temperatures along the length of the catalyst bed were measured by means of the aforementioned 13 stationary thermocouples, each of which was located along the first 99 inches of a 165-inch catalyst bed. The temperatures at the 3-inch and 75-inch locations were not available, since the thermocouples at those two locations had been damaged previously.

The results of these tests are presented hereinbelow in Tables IV, V and VI. The effect of TEP loading on hot spot temperature is summarized in Table IV. The effect of TEP loading on catalyst performance is presented in Table V. Catalyst bed temperature profiles obtained from the various tests of this example are listed in Table VI and are represented in the accompanying figures. The time on stream for each temperature profile is presented also in Table VI. Two temperature profiles are given for Test 2A. Test 2A and Test 2A' duplicated each other within very narrow limits and gave approximately the same results. The results shown for Test 2A also represent the results for Test 2A'.

TABLE IV

EFFECT OF ADDITION OF WATER AND ELEMENTAL PHOSPHORUS ON HOT SPOT TEMPERATURE WITH CATALYST A IN FLAMMABILITY RANGE

| Test | VHSV, hr-1 | N-$C_4$, mole % | lb TEP/ $10^5$ lb n-$C_4$ | Wgt. Ratio $H_2O$:P Added To Feed | Salt °C. | Hot Spot Temp. @C. | @F. |
|---|---|---|---|---|---|---|---|
| 1 | 1,650 | 1.61 | 9.3 | 29,400:1 | 425 | 490 | 914 |
| 1A | 1,650 | 1.61 | 18.6 | 14,700:1 | 432 | 463 | 865 |
| 2 | 1,550 | 1.72 | 9.3 | 29,400:1 | 423 | 482 | 900 |
| 2A | 1,550 | 1.72 | 18.6 | 14,700:1 | 432 | 467 | 872 |
| 3 | 1,450 | 1.85 | 9.3 | 29,400:1 | 425 | 471 | 880 |
| 3A | 1,450 | 1.85 | 18.6 | 12,600:1 | 432 | 470 | 877 |
| 4 | 1,350 | 1.98 | 9.3 | 22,000:1 | 421 | \multicolumn{2}{l|}{HOT SPOT RUNAWAY OCURRED} |
| 4A | 1,350 | 1.98 | 18.6 | 12,600:1 | 427 | 468 | 873 |
| 5 | 1,250 | 2.1 | 18.6 | 11,000:1 | \multicolumn{3}{l|}{HOT SPOT RUNAWAY OCCURRED} |

TABLE V

EFFECT OF ADDITION OF WATER AND ELEMENTAL PHOSPHORUS ON CATALYST PERFORMANCE WITH CATALYST A IN FLAMMABILITY RANGE

| Test | VHSV, hr-1 | n-C4, mole % | Wgt. Ratio $H_2O$:P Added To Feed | Conv. % | Selectivity, mole % | Yield, wt % |
|---|---|---|---|---|---|---|
| 1 | 1,650 | 1.61 | 29,400:1 | 83.5 | 63.5 | 89.3 |
| 1A | 1,650 | 1.61 | 14,700:1 | 80.2 | 68.6 | 92.7 |
| 2 | 1,550 | 1.72 | 29,400:1 | 82.3 | 66.2 | 91.9 |
| 2A | 1,550 | 1.72 | 14,700:1 | 82.4 | 67.9 | 94.4 |
| 3 | 1,450 | 1.85 | 29,400:1 | 82.8 | 65.9 | 92.0 |
| 3A | 1,450 | 1.85 | 12,600:1 | 84.8 | 67.3 | 96.3 |
| 4 | 1,350 | 1.98 | 22,000:1 | \multicolumn{3}{l|}{HOT SPOT RUNAWAY OCURRED} |
| 4A | 1,350 | 1.98 | 12,600:1 | 82.9 | 68.4 | 95.7 |
| 5 | 1,250 | 2.1 | 11,000:1 | \multicolumn{3}{l|}{HOT SPOT RUNAWAY OCCURRED} |

TABLE VI

CATALYST BED TEMPERATURE PROFILES (IN DEGREES F.)

| Test | 1 | 1A | 2 | 2A | 2A' | 3 | 3A | 4 | 4A |
|---|---|---|---|---|---|---|---|---|---|
| Hr on Str | 4,764 | 5,555 | 4,235 | 5,604 | 5,669 | 4,642 | 5,741 | 4,689 | 5,792 |
| Cat Bed Location | 425 | 449 | 408 | 453 | 431 | 427 | 464 | — | 440 |
| Preheat Zone | | | | | | | | | |
| 3 in | — | — | — | — | — | — | — | — | — |
| 9 in | 802 | 805 | 802 | 808 | 795 | 825 | 813 | — | 806 |
| 15 in | 842 | 828 | 844 | 831 | 816 | 837 | 835 | 840 | 829 |
| 21 in | 820 | 819 | 828 | 820 | 809 | 844 | 822 | (1) | 814 |
| 27 in | 809 | 815 | 810 | 815 | 805 | 817 | 816 | (1) | 808 |
| 33 in | 837 | 834 | 834 | 836 | 822 | 838 | 837 | (1) | 831 |
| 39 in | 877 | 855 | 870 | 860 | 842 | 865 | 862 | (1) | 860 |
| 51 in | 914 | 865 | 900 | 872 | 853 | 880 | 877 | (1000+) | 873 |
| 63 in | 866 | 858 | 844 | 862 | 850 | 847 | 868 | (1) | 854 |
| 75 in | — | (1) | — | — | — | — | — | (1) | — |
| 87 in | 804 | 834 | 803 | 835 | 826 | 806 | 838 | (1) | 827 |
| 99 in | 797 | 819 | 797 | 820 | 812 | 798 | 821 | (1) | 811 |

(1) Runaway temperature culminating at greater than 1000° F. at approximately 51 inches requiring immediate process shutdown to prevent catalyst meltdown.

Figure 2:
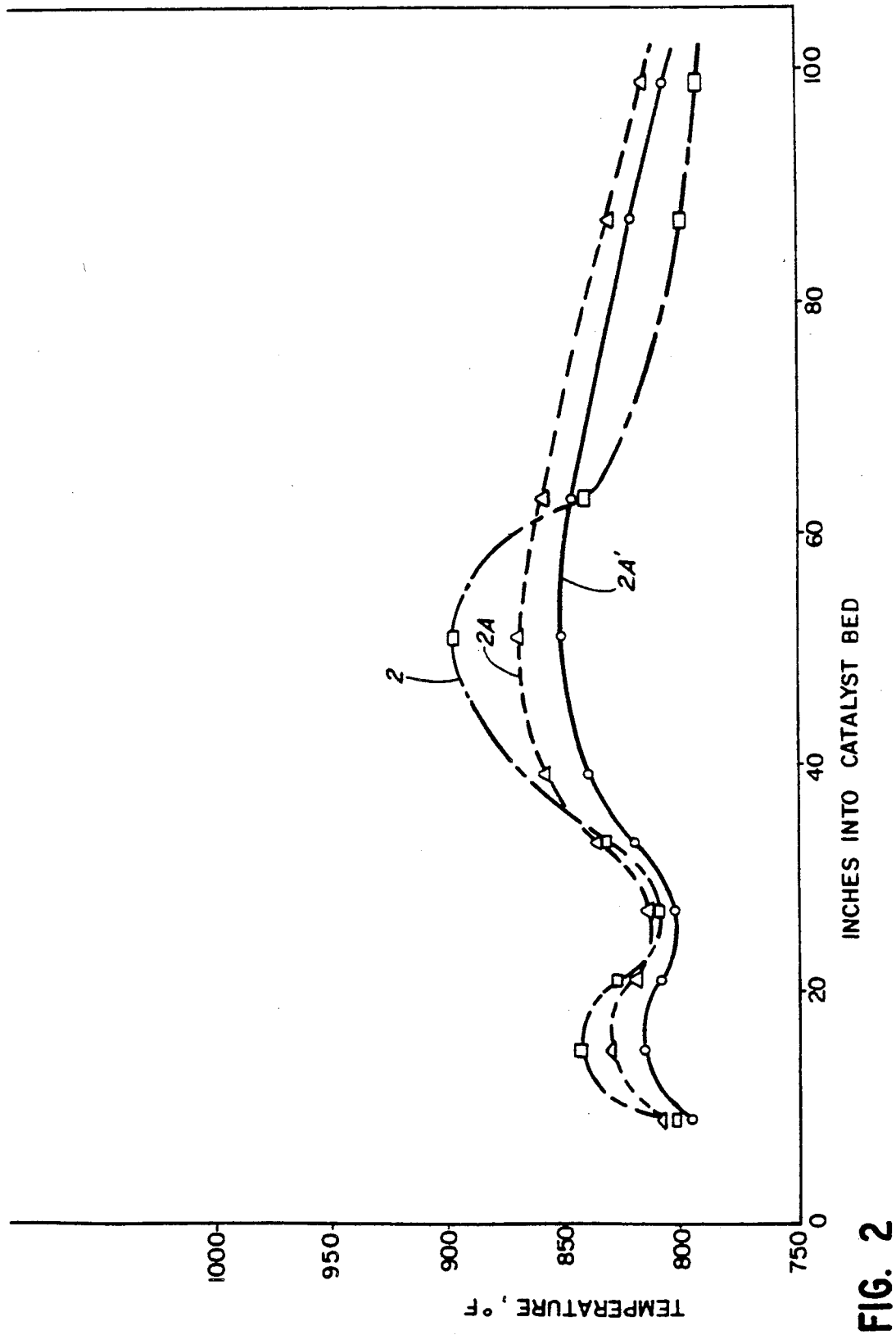
FIG. 2 illustrates the effect on the exotherm of the addition of solutions containing water and phosphorus in different ratios, decreased space velocity and increased n-butane concentration wherein the hot spot exotherm is diminished by decreasing the water-phosphorus ratio, and the overall temperature profile is more isothermal. Temperature profile 2 illustrates a temperature profile obtained with increased n-butane concentration over the n-butane concentration of FIG. 1 but with the same water-phosphorus ratio wherein the temperature gradient range is 57° C. (103° F.). Temperature profiles 2A and 2A' illustrate the temperature profile obtained wherein the ratio of phosphorus to water is increased to result in a more isothermal reaction wherein the temperature gradient range is 36° C. (64° F.) and 32° C. (58° F.).
Figure 3:
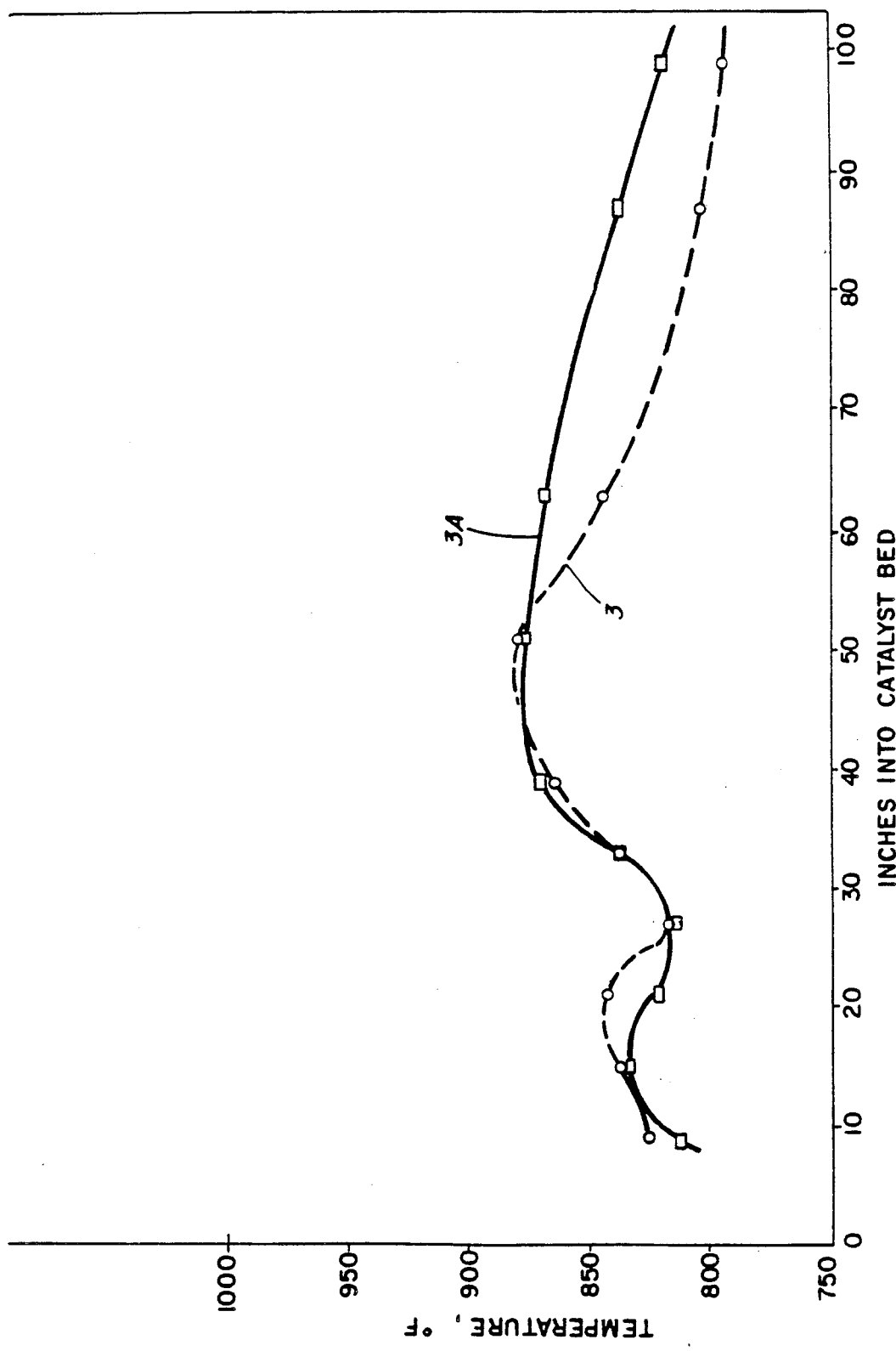
FIG. 3 illustrates two isothermal temperature profiles obtained with increased n-butane concentration, decreased space velocity and addition of water-phosphorus solutions in different ratios. Temperature profile 3A illustrates the effect of increasing phosphorus concentration over the water-phosphorus ratio of temperature profile 3 to achieve a more nearly isothermal temperature profile over that of temperature profile 3.
Figure 4:
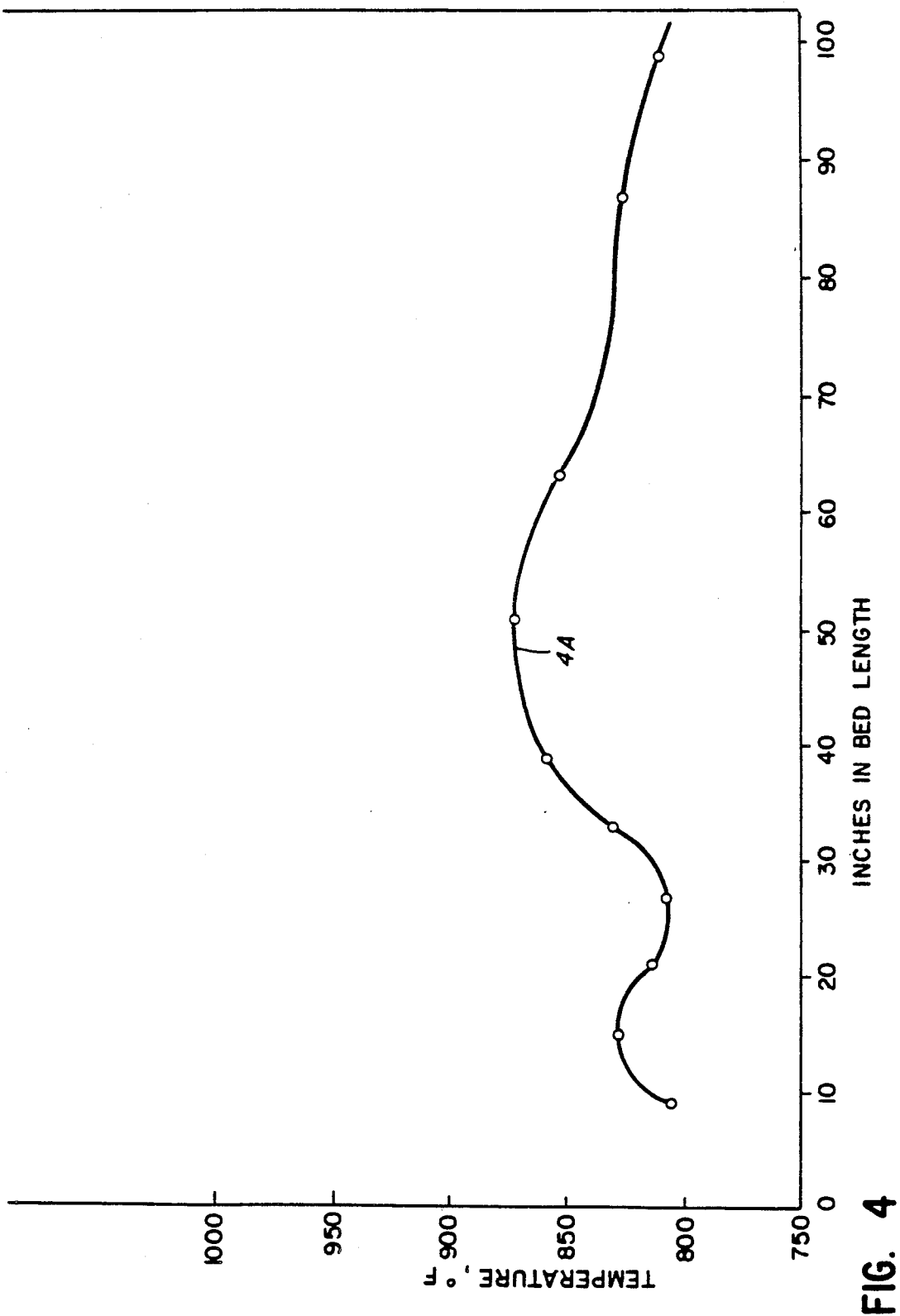
FIG. 4 illustrates a temperature profile obtained with a further increase of n-butane concentration, a further decrease in space velocity, but with the same concentration of water and phosphorus added to the reaction as in temperature profile 3A.

The accompanying figures provide comparisons of the catalyst bed temperature profiles obtained with the two TEP concentrations. FIG. 1 presents the temperature profiles obtained at VHSV of 1,650 hr$^{-1}$ and an n-butane concentration of 1.61 mole %; FIG. 2, the temperature profiles obtained at a VHSV of 1,550 hr$^{-1}$ and an n-butane concentration of 1.72 mole %; FIG. 3, the temperature profiles obtained at a VHSV of 1,450 hr$^{-1}$ and an n-butane concentration of 1.85 mole %; and FIG. 4, the temperature profiles obtained at a VHSV of 1,350 hr$^{-1}$ and an n-butane concentration of 1.98 mole %. Preheat zone temperatures are not shown in the figures. Please note that the two temperature profiles from Test 2A are identified in FIG. 2 as lines 2A and 2A'.

These temperature profiles demonstrate that the hot spot temperature was not shifted in the catalyst bed, but was decreased or suppressed, as TEP concentration in the feed was increased.

In general, the doubling in TEP loading at these larger n-butane concentrations resulted in a significant decrease in hot spot temperatures and concurrent increases in selectivity and yield. When the n-butane concentration was 1.98 mole % at the 9.3 TEP loading, the catalyst performance was erratic, the reactor operation became unstable, and hot spot runaway was observed. When the loading rate was doubled to 18.6 lb TEP/$10^5$ lb n-$C_4$, none of these problems occurred. However, when the TEP loading was 18.6 TEP/$10^5$ lb n-$C_4$ (8 ppm wt TEP), the n-butane concentration was 2.1 mole %, and the VHSV was 1,250 $hr^{-1}$, a hot spot runaway was observed.

FIGS. 1 to 4 demonstrate that as the ratio of water to phosphorus is decreased concurrently with a decrease in space velocity and an increase in n-butane concentration in the feed stream, the yield increases as the hot spot temperature decreases and the reaction zone temperature is more nearly isothermal throughout the reaction zone of a fixed bed reactor. The FIGS. 1 to 4 also demonstrate that as the temperature of the tail-out section of the catalyst bed is within an isothermal range of from zero degrees Fahrenheit to less than eighty degrees Fahrenheit of the hot spot temperature, overall product yield of the process increases to over 90 wt. %, i.e. the temperature difference or gradient between the hot spot temperature and the temperature of the tail-out section is from 0° to less than 80° F., or from 0° C. to less than 45° C.

According to the present invention, the water: phosphorus ratio in the feedstream must be precisely adjusted and controlled for a particular hydrocarbon concentration and space velocity in order to control the reaction zone temperature throughout the catalyst bed. Consistent yields of 90 wt. % or greater of product are thereupon obtained.

In summary, the instant invention comprises a continuous process for the partial oxidation of a hydrocarbon feedstock containing at least 1.6 mole percent n-butane to produce maleic anhydride, which process comprises contacting in a reaction zone said feedstock with an oxidant selected from the group consisting of molecular oxygen, air and an oxygen containing gas under oxidation conditions in the presence of an oxidation catalyst comprising vanadium, phosphorus and oxygen wherein atomic ratio of vanadium to phosphorus is in the range of from about 0.5:1 to about 1.25:1, and continuously adding to said feedstock water and an alkyl ester of orthophosphoric acid having the formula $(RO)_3P=O$ wherein the R is hydrogen or a $C_1$ to $C_4$ alkyl radical, at least one R being a $C_1$ to $C_4$ alkyl radical, wherein ratio by weight of said water to phosphorus in said alkyl ester is in the range of from about 6500:1 to about 50,000:1, water to phosphorus, in said feedstock wherein reaction temperature gradient throughout said reaction zone is from about 425° C. (797° F.) to about 470° C. (878° F.) and temperature differences between any hot spot temperature in the catalyst bed and the temperature of the tail-out section of said reaction zone is from 0° F. to less than about 80° F., or from 0° C. to less than about 45° C.

The alkyl ester can be selected from the group consisting of trimethylphosphate and triethylphosphate and the hydrocarbon feedstock can comprise n-butane. In further detail, the alkyl ester in a water solution can be added to the hydrocarbon feedstock prior to introduction of the feedstock into the reaction zone. Preferably, the ratio by weight of water to said phosphorus in the alkyl ester is in the range of from about 7000:1 to about 35,000:1 and the alkyl ester is triethylphosphate.

In more detail, the alkyl ester is triethylphosphate, the hydrocarbon feedstock comprises n-butane, the oxidant comprises air, reaction zone temperature is within the range of from about 425° C. (800° F.) to about 465° C. (870° F.) and oxidation conditions comprise an inlet pressure within the range of from about 1.68 atmos (10 psig) to about 3.72 atmos (40 psig), a VHSV within the range of from about 100 $hr^{-1}$ to about 4000 $hr^{-1}$, and a n-butane concentration in the range of from about 1.6 mole % to about 3.1 mole %.

What is claimed is:

1. A continuous process for the partial oxidation of a hydrocarbon feedstock comprising from about 1.6 to about 3.1 mole percent n-butane to produce maleic anhydride, which process comprises contacting in a reaction zone said feedstock with an oxidant selected from the group consisting of molecular oxygen, air, and other oxygen-containing gases under oxidation conditions in the presence of an oxidation catalyst comprising vanadium, phosphorus, and oxygen wherein atomic ratio of vanadium to phosphorus is in the range of from about 0.5:1 to about 1.25:1, and continuously adding to said feedstock, water and an alkyl ester of orthophosphoric acid having the formula $(RO)_3P=O$, wherein R is hydrogen of a $C_1$ to $C_4$ alkyl radical, at least one R being a $C_1$ to $C_4$ alkyl radical, wherein ratio by weight of said water to phosphorus is in the range of from about 6500:1 wt. to about 35,000:1 wt. water to phosphorus, wherein oxidation conditions comprise an inlet pressure within the range of from about 1.68 atoms (10 psig) to about 3.72 atmos (40 psig) and a VHSV within the range of from about 100 $hr^{-1}$ to about 4000 $hr^{-1}$ and wherein reaction temperature gradient throughout said reaction zone is from about 425° C. (797° F.) to about 470° C. (878° F.) and wherein the amounts of water and the alkyl ester of orthophosphoric acid are sufficient to provide temperature differences between any hot spot temperature in the catalyst bed and the temperature of the tail-out section of said reaction zone of from 0° F. to less than 80° F., or from 0° C. to less than 45° C.

2. The process of claim 1, wherein said alkyl ester is selected from the group consisting of trimethylphosphate and triethylphosphate.

3. The process of claim 1, wherein said alkyl ester in a water solution is added to said hydrocarbon feedstock prior to introduction of said feedstock into said reaction zone.

4. The process of claim 1, wherein said alkyl ester is triethylphosphate.

* * * * *